United States Patent [19]

Fabre et al.

[11] Patent Number: 5,376,379
[45] Date of Patent: Dec. 27, 1994

[54] LIPOSOMES OF THERMAL WATERS STABILIZED IN A DNA GEL

[75] Inventors: Pierre Fabre, Castres; Henri Cousse, Chemin de Lastinos; Gilbert Mouzin, Toulouse; Marie-Thérése Trebosc, Castres, all of France

[73] Assignee: Pierre Fabre Cosmetique, Boulogne, France

[21] Appl. No.: 66,111

[22] PCT Filed: Oct. 16, 1991

[86] PCT No.: PCT/FR91/00805

§ 371 Date: Jun. 4, 1993

§ 102(e) Date: Jun. 4, 1993

[87] PCT Pub. No.: WO92/06666

PCT Pub. Date: Apr. 30, 1992

[30] Foreign Application Priority Data

Oct. 17, 1990 [FR] France .................... 90 12811

[51] Int. Cl.⁵ ............................. A61K 9/127

[52] U.S. Cl. ................... 424/450; 424/401; 428/402.2

[58] Field of Search .............. 424/450, 401; 428/402.2

[56] References Cited

U.S. PATENT DOCUMENTS 5,244,672 9/1993 Huc et al. .................... 424/450

FOREIGN PATENT DOCUMENTS 2511243 2/1983 France .
2609393 7/1988 France .
3061859 3/1991 Japan .

Primary Examiner—G. S. Kishore
Attorney, Agent, or Firm—Jacobson, Price, Holman & Stern

[57] ABSTRACT

The present invention relates to compositions based on thermal water containing liposomes of thermal water stabilized in a deoxyribonucleic acid (DNA) gel and a process for preparing thereof. The composition is useful in dermatology and cosmetology.

13 Claims, No Drawings

LIPOSOMES OF THERMAL WATERS STABILIZED IN A DNA GEL

The present invention relates to compositions based on thermal water containing liposomes of thermal water stabilized in a DNA gel, which are useful especially in dermatology and in cosmetology. Liposomes are microvesicles consisting of one or more lipid double layers delimiting a central aqueous space and, in the case of multilamellar liposomes, an aqueous behavior between two double layers.

These structures consist of phospholipids to which sterols such as cholesterol are frequently added in order to increase the stability.

Liposomes may be classified according to their size and their uni- or multilammelar character.

| | |
|---|---|
| MLV (multilammelar vesicles): | diameter 100 to 5000 nm (several double layers) |
| LUV (large unilammelar vesicles): | diameter 200 to 2000 nm (1 double layer) |
| SUV (small unilammelar vesicles): | diameter 20 to 80 nm (1 double layer) |

Techniques enabling large quantities of liposomes to be obtained have been developed in industry (ultra-dispersion, sonication, lipopred.) ref. PUISIEUX F., DELATTRE J.—Les liposomes. Application thérapeutiques, Technique et Documentation, Lavoisier Paris, 1985.

These microvesicles are capable of interacting with cells whose membranes are identical in nature to that of the liposome.

Dermatology and cosmetology constitute promising sectors for the exploitation of liposomes.

The principal studies relating to the skin relate to the liposomes of corticoids. It would appear that the microencapsulation of corticoids reduces the percutaneous penetration of the product and increases its concentration at local sites : epidermis and dermis. Ref. WOHLRAB W., LASCH J.—Penetration Kinetics of liposomal hydrocortisone in human skin. Dermatologica 174, 18-22, 1987.

Other substances have been incorporated but the studies are too fragmented to be generalized: EGF (Epidermal Growth Factor) is thought to promote the cicatrization of wounds : superoxide dismutases are thought locally to have an anti-inflammatory action. Unfortunately, the liposome vesicles are too fragile in the formulations used and they are often destroyed before reaching their target.

Many others have mentioned the use of gelling agents to stabilize liposomal vesicles in the form of an aqueous gel.

The principal gelling agents used are: gelatin, carboxyvinyl polymers, methacrylic polymers, polydimethylsiloxane copolymers and, more recently, collagen.

The stabilization of the liposomes in an aqueous gel with the gelling agents currently used does not make it possible to obtain a stability of a formula greater than 3 months at a temperature of 40° C.

The present invention makes it possible to overcome this major disadvantage by stabilizing the liposomes in a deoxyribonucleic acid gel.

According to the invention, the DNA will be DNA which is highly polymerized according to processes known to persons skilled in the art (hereinafter "HP DNA") and which is available commercially.

There may be mentioned in particular DNA having a molecular mass of between 500,000 and 1.5 million, preferably between 800,000 and 1.2 million.

The composition according to the invention advantageously contains 0.1 to 10% by weight of DNA and more particularly 0.5 to 5%.

According to the invention, thermal water, and more particularly AVENE water or CAUTERETS water, is incorporated into the liposomes. AVENE water has therapeutic qualities which are useful in the treatment of eczemas, pruritus, psoriasis, retardation of cicatrization, burns. Basic studies have also supported the effectiveness of AVENE WATER. Thus, several series of studies have made it possible to demonstrate that AVENE WATER exerts an inhibitory effect on the degranulation of human basophiles. It also inhibits the migration of polynuclear cells which have an important role in skin inflammation.

Sulfurated CAUTERETS water, in the form of liposomes, is of interest in dermatology and more particularly in the following treatments: psoriasis, eczemas, acne, pruritus, seborrhoea, alopecia.

The composition of AVENE WATER is as follows:

| | mg/l |
|---|---|
| ANION | |
| $HCO_3^-$ (bicarbonates) | 218.4 |
| $Cl^-$ (chlorides) | 5.8 |
| $SO_4$ (sulfates) | 12.4 |
| $NO_3$ (nitrates) | 1.1 |
| $NO_2$ (nitrites) | <0.02 |
| $F^-$ (fluorides) | 0.12 |
| $PO_4$ (phosphates) | <0.1 |
| $Br^-$ (bromides) | <0.1 |
| CATIONS | |
| $Ca^{++}$ (calcium) | 40.8 |
| $Mg^{++}$ (magnesium) | 22.7 |
| $K^+$ (potassium) | 1.0 |
| $Na^+$ (sodium) | 4.8 |
| $Li^+$ (lithium) | <0.1 |
| $Fe^{++}$ (iron) | <0.01 |
| $Mn^{++}$ (manganese) | <0.0005 |
| $Sr^{++}$ (strontium) | 0.13 |

The composition of CAUTERETS water is as follows:

| | mg/l |
|---|---|
| ANION | |
| $HCO_3$ (bicarbonates) | 25 |
| $CO_3$ (carbonates) | 23.4 |
| $H_3SiO_4^-$ (silicates) | 32.8 |
| $Cl^-$ (chlorides) | 45 |
| $SO_4^{2-}$ (sulfates) | 31.5 |
| $NO_2^-$ (nitrites) | — |
| $NO_3^-$ (nitrates) | — |
| $PO_4^{3-}$ (phosphates) | — |
| $F^-$ (fluorides) | 2.2 |
| $HS^-$ (sulfides) | trace amounts |
| $SO_3^{2-}$ (sulfites) | trace amounts |
| $S_2O_3^{2-}$ (thiosulfate) | 5.6 |
| CATIONS | |
| $Ca^{2+}$ (calcium) | 5 |
| $Mg^{2+}$ (magnesium) | 0.12 |
| $Na^+$ (sodium) | 63.6 |
| $K^+$ (potassium) | 1.8 |
| $NH_4^+$ (ammonium) | |

-continued

|  | mg/l |
|---|---|
| $Mn^{2+}$ (manganese) | |
| $Al^{3+}$ (aluminum) | |
| $Zn^{2+}$ (zinc) | |
| $Cu^{2+}$ (copper) | |
| $Li^+$ (lithium) | 0.18 |

Naturally, according to the present invention, any other thermal water of therapeutic and/or cosmetic interest may also be microencapsulated so as to allow a targeted penetration of these waters into the epidermis and the dermis.

According to an additional characteristic of the present invention, the composition optionally contains, in addition, an associated active ingredient such as an antibacterial agent and more particularly phenonip, EDTA, benzoic acid, butyl para hydroxybenzoate, sorbic acid, an associated vitamin ingredient such as vitamin E, vitamin C, or alternatively, an oil such as borage oil or argan oil.

Naturally, the above list is not limiting.

This associated active ingredient will thus be present in particular in an amount of 0 of 5% and more often 0.1 to 3% by weight of the composition.

The composition according to the present invention advantageously contains 0.1 to 10% by weight of lipids entering into the constitution of the liposomes and more particularly 0.5 to 5%, the (lipid)/(liposome-encapsulated thermal water) weight ratio is about ⅓.

In one embodiment, the liposomes used in the present invention are of the multilamellar type, prepared according to French Patent 2,634,375.

In this particular embodiment, the liposome gels are prepared in the following manner:

a) liposomes

A lipid phase consisting essentially of a solution of amphiphilic lipids and optionally a said associated active ingredient of lipophilic nature is prepared in an organic solvent and more particularly ethanol.

This phase is then added, with gentle stirring, to a solution of thermal water optionally containing a said associated ingredient of hydrophilic nature.

After evaporation under reduced pressure, a suspension of desired liposome concentration is obtained.

The amphiphilic lipids may be glycolipids, phosphoamino lipids and especially phospholipids, for example lecithins (of egg, soya bean, and the like).

The solvent is preferably an alcohol which is miscible with water in all proportions, especially ethanol.

The solution of amphiphilic lipids may contain, in addition, a substance of lipophilic nature designed to modify the physical characteristics (electric charge, rigidity) or the chemical characteristics of the wall, such as cholesterol, stearylamine, phosphatidic acid and the like.

The concentration of lipids in the solvent may be 0.1 to 10% by weight, preferably 1 to 5% by weight.

It is advantageous that the volume of solvent used for phase (1) is between 30 and 100%; for example about 50%, of the volume of water of phase (2), in order to obtain liposomes of small size (especially from 100 to 300 nm).

Thus, the invention makes it possible to obtain medicinal products, especially in injectable form, and cosmetic products which are very stable.

b) preparation of the liposome gel

To the above suspension are added, with gentle stirring, DNA (especially HP DNA) as well as, optionally, preservatives and perfumes.

The invention makes it possible to obtain liposomes of thermal water which are perfectly stable in a gel.

These formulations obtained according to the present invention may be used in dermocosmetology especially by topical application when the composition contains a vehicle for topical application, it may be a gel packaged in a tube or in a pump-based mechanical system, or a spray composition delivered in the form of a gel.

The following examples are intended to illustrate the invention without, however, being of a limiting nature.

EXAMPLE 1

Preparation of a 5 kg batch of liposomes of AVENE water containing 2% lipids.

Raw material

| 1 - organic phase | |
|---|---|
| phospholipid (Lipoid 80)o [sic] SEPPIC | 100 g |
| Cholesterol BP | 15 g |
| Ethanol 95% | 2.5 liters |
| 2 - aqueous phase | |
| AVENE water | 5 liters |
| EDTA, disodium | 10 g |

Procedure

1—Preparation of the organic phase I

Into 2.5 liters of ethanol are introduced, with vigorous stirring at room temperature, 100 g of phospholipid, 10 g of cholesterol and 10 g of phenonip. The stirring is continued for ½ hour until dissolution and production of a pale yellow homogeneous phase.

2—Preparation of the aqueous phase

Into 5 liters of Avene water are introduced, with stirring, 10 g of disodium EDTA.

3—Preparation of the liposomes

The organic phase I is introduced into the aqueous phase II in thin jets by means of a Kremlin apparatus and a peristaltic pump.

The addition, with vigorous stirring, by means of a Rayneri apparatus lasts for 15 min. The organic phase should be introduced outside the stirring cone. A milky phase is formed.

2.7 liters (ethanol+water) are evaporated under reduced pressure. The temperature of the water bath is 50° C. A 4.8-liter milky solution is obtained containing 2% lipids which is adjusted to 5 liters with AVENE water.

EXAMPLE 2

Preparation of the composition of liposomes of thermal water stabilized by an HP DNA gel.

To the above milky solution containing 2% lipids are added, with gentle stirring and in small fractions, 100 g of Hp DNA (marketed by the company JAVERNECH). The dissolution is carried out slowly at room temperature. After stirring for 1 hour, a stabilized formulation is obtained containing 2% Hp DNA gel and 2% liposomes.

EXAMPLE 3

Formulations

In the formulations below, the quantity (by weight) of thermal water encapsulated in the liposomes is of the order of 3 times that of the lipids which constitute the liposomes.

| FORMULATION 1: | |
|---|---|
| Lipids | 2% |
| HP DNA | 2% |
| Phenonip | 0.5% |
| EDTA | 0.2% |
| Avene water q.s. | 100 |
| FORMULATION 2: | |
| Lipids | 2% |
| HP DNA | 0.5% |
| Phenonip | 0.5% |
| EDTA | 0.2% |
| Avene water q.s. | 100 |
| FORMULATION 3: | |
| Lipids | 2% |
| HP DNA | 0.1% |
| Phenonip | 0.5% |
| EDTA | 0.2% |
| Avene water q.s. | 100 |
| FORMULATION 4: | |
| Lipids | 0.5% |
| HP DNA | 0.2% |
| Butyl para-hydroxybenzoate | 0.2% |
| Floral water | 1% |
| Avene water q.s. | 100 |
| FORMULATION 5: | |
| Lipids | 2% |
| HP DNA | 0.5% |
| Sorbic acid | 0.3% |
| Cauterets water q.s. | 100 |
| FORMULATION 6: | |
| Lipids | 1% |
| HP DNA | 0.5% |
| Vitamin C | 1% |
| Phenonip | 0.5% |
| Floral water | 1% |
| Cauterets water q.s. | 100 |
| FORMULATION 7: | |
| Lipids | 2% |
| HP DNA | 0.5% |
| Ginkgo extract | 1% |
| Phenonip | 0.5% |
| Floral water | 1% |
| Thermal water q.s. | 100 |
| FORMULATION 8: | |
| Lipids | 0.1% |
| HP DNA | 0.5% |
| Borage oil | 1% |
| Phenonip | 1% |
| Thermal water q.s. | 100 |
| FORMULATION 9: | |
| Lipids | 10% |
| HP DNA | 5% |
| Vitamin E | 0.5% |
| Phenonip | 1% |
| Thermal water q.s. | 100 |

EXAMPLE 4

Stability study

The stability study was carried out at 40° C. on formulations containing 2% liposomes of Avene thermal water.

The visualization was performed using an electron microscope, this visualization is carried out each month after subjecting the liposomes to negative staining by means of a 2% solution of sodium phosphotungstate.

The results of this study are summarized in the following table:

| gelling agent | Time/month | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Gelatin 5% | + | ± | − | | | | | | | | | |
| Carbopol 941 (0.5%) | + | + | ± | − | | | | | | | | |
| Carbopol 910 (0.5%) | + | + | ± | − | | | | | | | | |
| Endispert HV (0.5%) | + | + | + | ± | − | | | | | | | |
| Endispert MV (0.5%) | + | + | ± | − | | | | | | | | |
| Dimethycone copolyol (2%) | + | + | + | ± | − | | | | | | | |
| Collagen (5%) | + | + | + | ± | − | | | | | | | |
| HP DNA (0.1%) | + | + | +̲ | +̲ | +̲ | +̲ | +̲ | +̲ | ± | + | | |
| HP DNA (0.5%) | + | + | + | + | + | + | + | + | + | + | + | + |
| HP DNA (2%) | + | + | + | + | + | + | + | + | + | + | + | + |

+ = Good stability (liposome 300 + 30 nm)
+̲ = Increase in size of the liposomes (by membrane fusion)
− = Phase separation (instability of the formula).

The photographic examinations show that the liposomes are correctly dispersed in an HP DNA lattice without modification of their shape and their size and confirms the surprising stability of the liposomes in base formulation.

From the other experiments carried out, the result is reached that the presence of DNA according to the invention makes it possible to obtain a remarkable stabilization of the liposomes of mineral water according to the invention during their preparation as well as in the galenical formulations.

An H.P. DNA level of 0.5 to 2% makes it possible to stabilize the liposomes for 24 months, whereas with the conventional gelling agents of the Carbopol and/or Collagen type, the stability of the liposomal membranes is maintained for a maximum of 6 months.

This stability may be explained by the crosslinkage of the H.P. DNA fibers in aqueous medium which allows the dispersion of the liposomes and prevents the fusion of the lipid vesicles.

EXAMPLE 5

Pharmaceutical and chemical activity

The vectorization of mineral water in liposomal form according to the invention makes it possible, surprisingly, to potentiate the pharmacological and clinical activity of this water.

The results obtained are summarized below.

1. Inhibition of the degranulation of human basophiles

The degranulation of human basophiles is examined according to the following procedure:

Production of basophiles sensitized to a given antigen from samples from allergic patients or after passive sensitization of basophiles of donors with a serum rich in specific IgE antibodies.

When the sensitized basophiles are obtained from allergic patients, it is necessary to carry out an enrichment by mere sedimentation at 1 g and centrifugation of the leucocyte-rich plasma. The leucocytic pellet contains 1500 to 3000 basophiles/mm³.

The leucocytes obtained are then suspended in an inorganic buffer and then centrifuged. The sensitizing antigen is then diluted in RPMI 1640 (flows Labo) (7 5-fold serial dilutions) starting with a concentration of for example 10-3 in the case of glycerinated extracts.

To study the vectorization of Avene water on this sensitizing basophile-allergen, pure water and distilled water are placed in contact with an aliquot of the cell pellet and incubated for 30 min at 25° C. After this incubation time, the cell suspension is mixed in equal volumes with the dilutions of the antigen, plus a control without antigen.

The cell-antigen mixture is incubated for 15 min at 37° C. and then stained with toluidine blue.

The non-degranulated basophiles are then counted in Malassez or Fuchs-Rosenthal hemocytoniters.

Results

The table below shows the results expressed in maximum percentage of degranulation for 15 degranulation tests in the presence of various pneumallergens. The average percentage of degranulation for the 15 experiments is 57.1% for the distilled water controls, 29.3% for Avene water and 14.1% for the tests carried out with stabilized liposomes. (This difference is highly significant $p < 0.01$).

| Distilled water | Avene Water | Avene water liposomes H.P. DNA (5%) |
|---|---|---|
| 57.1% | 29.3% | 14.1% |

Conclusion

The vectorization of Avene water by the liposomes allows a 100% potentiation of the inhibitory effect of the degranulation of the basophiles.

2. Pharmacoclinical study

A potentiation of the anti-irritant activity in man was studied using a model of skin irritation caused by Sodium Lauryl Sulfate (SLS).

Products tested
(a) Distilled water
(b) Avene water
(c) Avene water (liposomes H.P. DNA—5%)

The three products to be studied are used as solvent for SLS in order to prepare solutions at the same concentration as the control SLS solution which constitutes the model of irritation. They are applied together with the control on the occlusive patch test, for 24 hours.

The evaluation of the intensity of skin irritation is carried out by measuring the variations in skin blood flow by Doppler Laser Velocimetry (DLV).

Procedure (number of subjects: 20)

Three SLS solutions at 0.75% are prepared using the products to be studied (a-b-c). The control SLS solution and the a, b and c solutions are applied in a random manner in an amount of 65 $\mu l/cm^3$ on a disk of filter paper.

An occlusive dressing is then maintained for 24 hours. After removing the dressings, the skin is left in the open air for 30 min before starting the measurements so as to eliminate any possible effect of the occlusion.

The measurement of the skin blood flow is carried out by recording the DLV for 10 min on each area, on the one hand, before application of the patches, so as to obtain the physiological baseline and, on the other hand, 30 min after removing the patches.

The results are expressed by the mean of the area under the curve.

The percentage inhibition of inflammation by SLS is calculated by means of the following formula:

$$\% = \frac{AUC\ SLS - AUC\ p}{AUC\ SLS} \cdot 100$$

AUC SLS = area under the curve for the solution of SLS alone

AUC p = area under the curve for the solutions of the products a, b and c

To determine whether the activity of the products studied is significant, a statistical study using the paired Student's t test is carried out on the results obtained.

Results

Percentage inhibition of the irritation induced by SLS

| a | b | c |
|---|---|---|
| 14 NS | 39.8 (S) | 82.2 (S) |

The clinical study confirms the very clear potentiation (>100%) of the anti-inflammatory activity of Avene water vectorized by liposomes.

We claim:

1. A composition based on thermal water comprising liposomes encapsulating thermal water and said liposomes stabilized in a deoxyribonucleic acid (DNA) gel.

2. The composition according to claim 1 wherein the deoxyribonucleic acid is highly polymerized (HP DNA).

3. The composition according to claim 1 wherein it contains 0.1 to 10% DNA.

4. The composition according to claim 1 further comprising an active ingredient.

5. The composition according to claim 4 wherein the active ingredient is selected from a group consisting of vitamin E, vitamin C, borage oil, argan oil and a ginkgo biloba extract.

6. The composition according to claim 4 wherein the composition contains 0.1 to 3% by weight of the said associated active ingredient.

7. The composition according to claim 1 further comprising one or more vehicles appropriate for use in cosmetology.

8. A process for the preparation of a composition containing a liposome gel comprising the following steps:
   1) Preparing a lipid phase comprising a solution of amphiphilic liquids in an organic solvent;
   2) Adding the lipid phase with gentle stirring, to a solution of thermal water containing a said associated active ingredient of hydrophilic;
   3) Evaporating under reduced pressure the liquid phase and thermal water to obtain a suspension of desired liposome concentration; and
   4) Introducing DNA into the suspension with gentle stirring.

9. The composition according to claim 4 wherein the associated active ingredient is an antibacterial agent.

10. The composition according to claim 9 wherein the antibacterial agent is selected from a group consisting of phenonip, EDTA, benzoic acid, butyl para-hydrobenzoate and sorbic acid.

11. The method according to claim 8 further comprising the addition of an active ingredient of lipophilic nature in step 1.

12. The method according to claim 8 wherein the organic solvent in step 1 is ethanol.

13. The method according to claim 8 further comprising the addition of an active ingredient of hydrophilic nature in step 2.

* * * * *